United States Patent
Day et al.

(10) Patent No.: US 10,467,798 B2
(45) Date of Patent: Nov. 5, 2019

(54) RENDERING A GLOBAL ILLUMINATION IMAGE FROM A VOLUMETRIC MEDICAL IMAGING DATA SET

(71) Applicant: Toshiba Medical Systems Corporation, Otawara-shi (JP)

(72) Inventors: Timothy Day, Edinburgh (GB); Magnus Wahrenberg, Edinburgh (GB); Steven Reynolds, Edinburgh (GB); Gerald Chau, Edinburgh (GB); Andy Smout, Edinburgh (GB)

(73) Assignee: Canon Medical Systems Corporation, Otawara-shi (JP)

( * ) Notice: Subject to any disclaimer, the term of this patent is extended or adjusted under 35 U.S.C. 154(b) by 4 days.

(21) Appl. No.: 15/383,114

(22) Filed: Dec. 19, 2016

(65) Prior Publication Data

US 2018/0174355 A1    Jun. 21, 2018

(51) Int. Cl.
*G06T 15/08*    (2011.01)
*G09G 5/10*    (2006.01)
(Continued)

(52) U.S. Cl.
CPC .............. *G06T 15/08* (2013.01); *A61B 6/461* (2013.01); *A61B 6/466* (2013.01); *A61B 8/461* (2013.01);
(Continued)

(58) Field of Classification Search
CPC .............................. G06T 15/08; A61B 5/0059
See application file for complete search history.

(56) References Cited

U.S. PATENT DOCUMENTS 6,662,031 B1* 12/2003 Khalil ................. A61B 5/0059
                                                            600/310
8,659,602 B2   2/2014 Masumoto et al.
(Continued)

FOREIGN PATENT DOCUMENTS

JP           9-6986         1/1997
JP       2008-259699       10/2008
(Continued)

OTHER PUBLICATIONS

"Blender 2.78 Manual", Blender Manual, https://www.blender.org/manual/render/blender_render/materials/properties/preview.html. 2016, 1 page.
(Continued)

*Primary Examiner* — Mark K Zimmerman
*Assistant Examiner* — Jonathan M Cofino
(74) *Attorney, Agent, or Firm* — Oblon, McClelland, Maier & Neustadt, L.L.P.

(57) ABSTRACT

An image rendering apparatus includes processing circuitry to obtain a volumetric medical imaging data set representative of a region of a material; associate one particular extinction color with the material; determine, based on the particular extinction color, a chromatic attenuation profile representative of color value as a function of intensity and as a function of depth in the material, the chromatic attenuation profile showing how the material having the particular extinction color changes in appearance with changes in the depth; obtain, from a user, a color value; determine a modified extinction color for the material based on the color value obtained from the user; and render a global illumination image from the volumetric medical imaging data set using the modified extinction color.

19 Claims, 5 Drawing Sheets

(51) Int. Cl.
*A61B 6/00* (2006.01)
*A61B 8/00* (2006.01)
*G01N 29/06* (2006.01)
*G01S 7/52* (2006.01)
*G01S 15/89* (2006.01)
*G09G 5/04* (2006.01)
*G09G 5/40* (2006.01)
*A61B 6/03* (2006.01)

(52) U.S. Cl.
CPC ......... *A61B 8/466* (2013.01); *G01N 29/0609* (2013.01); *G01S 7/52071* (2013.01); *G01S 15/8993* (2013.01); *G09G 5/04* (2013.01); *G09G 5/10* (2013.01); *G09G 5/40* (2013.01); *A61B 6/032* (2013.01); *A61B 6/037* (2013.01); *A61B 8/467* (2013.01); *G06T 2210/41* (2013.01); *G09G 2340/06* (2013.01); *G09G 2380/08* (2013.01)

(56) References Cited

U.S. PATENT DOCUMENTS

| | | | | |
|---|---|---|---|---|
| 2008/0055305 | A1* | 3/2008 | Blank | G06T 15/08 345/419 |
| 2008/0259080 | A1* | 10/2008 | Masumoto | G06T 15/08 345/426 |
| 2008/0267467 | A1 | 10/2008 | Sokulin et al. | |
| 2009/0174729 | A1 | 7/2009 | Matsumoto | |
| 2010/0272344 | A1* | 10/2010 | Ichihara | A61B 6/032 382/132 |
| 2011/0172531 | A1* | 7/2011 | Kanayama | A61B 8/461 600/443 |
| 2014/0105476 | A1* | 4/2014 | Bulumulla | G06K 9/00 382/131 |
| 2014/0114189 | A1* | 4/2014 | Kanayama | G01S 7/52046 600/438 |
| 2014/0232719 | A1* | 8/2014 | Wahrenberg | G06T 15/506 345/424 |
| 2014/0375631 | A1* | 12/2014 | Masumoto | G06T 15/08 345/419 |
| 2015/0029185 | A1* | 1/2015 | Ikits | G06T 15/08 345/420 |
| 2015/0164475 | A1 | 6/2015 | Kuga et al. | |
| 2015/0355300 | A1* | 12/2015 | Ooshima | G01R 33/5608 324/309 |

FOREIGN PATENT DOCUMENTS

| | | |
|---|---|---|
| JP | 2008-272473 | 11/2008 |
| JP | 2009-160306 | 7/2009 |
| JP | 2014-61288 | 4/2014 |
| JP | 2015-132509 | 7/2015 |

OTHER PUBLICATIONS

Andrej Varchola "Live Fetoscopic Visualization of 4D Ultrasound Data", Dissertation, Tu Wien, Chapter 5, 2012, 46 pages.
Stefan Bruckner "From Static to Dynamic, Visualization of Real-Time Imaging Data", University of Bergen, 78 pages.

* cited by examiner

RENDERING A GLOBAL ILLUMINATION IMAGE FROM A VOLUMETRIC MEDICAL IMAGING DATA SET

FIELD

Embodiments described herein relate generally to a method of, and apparatus for, image rendering, for example image rendering using global illumination.

BACKGROUND

It is known to render images from volumetric imaging data, for example from volumetric medical imaging data. A set of volumetric imaging data may be referred to as an image volume. The set of volumetric imaging data may comprise a plurality of voxels with associated intensities, with each voxel being representative of a corresponding spatial location in a medical imaging scan.

Direct Volume Rendering (DVR) is a method for volume rendering. DVR may be considered to be an industry standard for volume rendering.

DVR renders a volumetric imaging data set by modelling a cloud of emissive material. Each point in a volume represented by the volumetric imaging data set is assigned properties of color and opacity. The color and opacity may be expressed as RGBA values, where R is red, G is green, B is blue and A is alpha. Alpha may be a measure of opacity in which a value of 0% indicates transparency and a value of 100% indicates full opacity.

Global illumination (GI) is a further method for volume rendering. Global illumination rendering has more degrees of freedom than DVR. In global illumination, a lighting model may be used that includes both direct illumination by light coming directly from a light source and indirect illumination, for example illumination by light that has been scattered from another surface.

In global illumination, each point in the volume is assigned a property that may be referred to as an extinction color, absorption color, or attenuation color. In the description below we use the term extinction color. The extinction color may be expressed as an RGB color.

The extinction color for a point in the volume is representative of the color-dependent absorption of light at that point in the volume. The use of extinction colors may enable realistic tissue effects due to chroma-dependent attenuation. For example, white light passing through human tissue may become redder as it passes through the tissue due to the tissue preferentially absorbing blue and green components of the white light. The use of extinction colors may allow such reddening, and other tissue effects, to be rendered.

BRIEF DESCRIPTION OF THE DRAWINGS

Embodiments are now described, by way of non-limiting example, and are illustrated in the following figures, in which.

DETAILED DESCRIPTION

Certain embodiments provide an image rendering apparatus comprising processing circuitry configured to: obtain a volumetric medical imaging data set representative of a region of a material; associate an extinction color with the material; obtain from a user a color value; determine a modified extinction color for the material based on the color value obtained from the user; and render a global illumination image from the volumetric medical imaging data set using the modified extinction color.

Certain embodiments provide an image rendering method comprising: obtaining a volumetric medical imaging data set representative of a region of a material; associating an extinction color with the material; obtaining from a user a color value; determining a modified extinction color for the material based on the color value obtained from the user; and rendering a global illumination image from the volumetric medical imaging data set using the extinction color.

Figure 1:
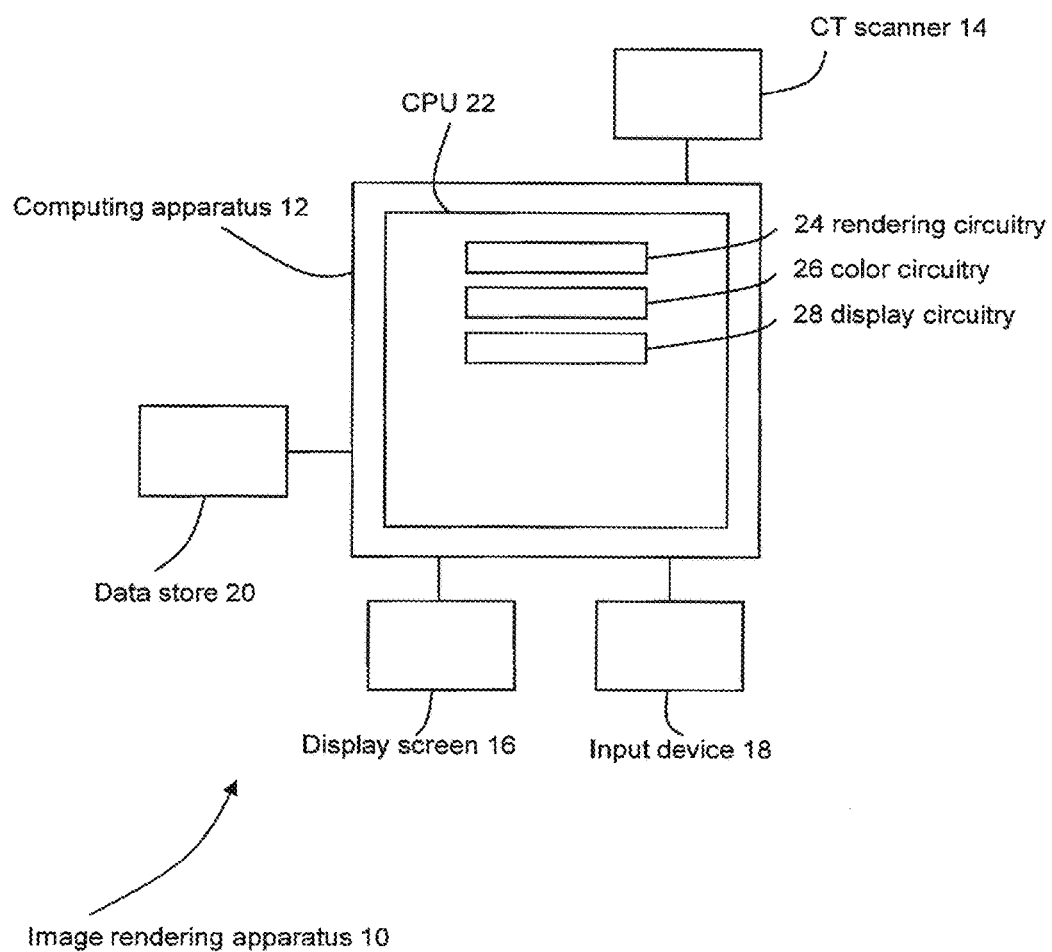
FIG. 1 is a schematic diagram of an apparatus according to an embodiment.

An image rendering apparatus 10 according to an embodiment is illustrated schematically in FIG. 1. The image rendering apparatus 10 comprises a computing apparatus 12, which in this case is a personal computer (PC) or workstation. The computing apparatus 12 is connected to a CT scanner 14, a display screen 16 and an input device or devices 18, such as a computer keyboard and mouse.

In other embodiments, the CT scanner 14 may be supplemented or replaced by a scanner in any appropriate imaging modality, for example a cone-beam CT scanner, MRI (magnetic resonance imaging) scanner, X-ray scanner, PET (position emission tomography) scanner, SPECT (single photon emission computed tomography) scanner, or ultrasound scanner.

In the present embodiment, sets of volumetric imaging data are obtained by the CT scanner 14 and stored in data store 20. The image rendering apparatus 10 receives sets of volumetric imaging data from data store 20.

In other embodiments, sets of image data may be obtained by any suitable scanner and stored in data store 20. In alternative embodiments, the image rendering apparatus 10 receives sets of volumetric imaging data from a remote data store (not shown) which may form part of a Picture Archiving and Communication System (PACS). The image rendering apparatus 10 may not be connected to a scanner 14.

Computing apparatus 12 provides a processing resource for automatically or semi-automatically processing volumetric imaging data sets. Computing apparatus 12 comprises a central processing unit (CPU) 22.

The computing apparatus 12 includes rendering circuitry 24 configured to render medical images from volumetric imaging data, color circuitry 26 configured to determine color values including extinction color values, and display circuitry 28 configured to display an interface and a rendered image to a user.

In the present embodiment, the circuitries 24, 26, 28 are each implemented in computing apparatus 12 by means of a computer program having computer-readable instructions that are executable to perform the method of the embodiment. However, in other embodiments, the various circuitries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
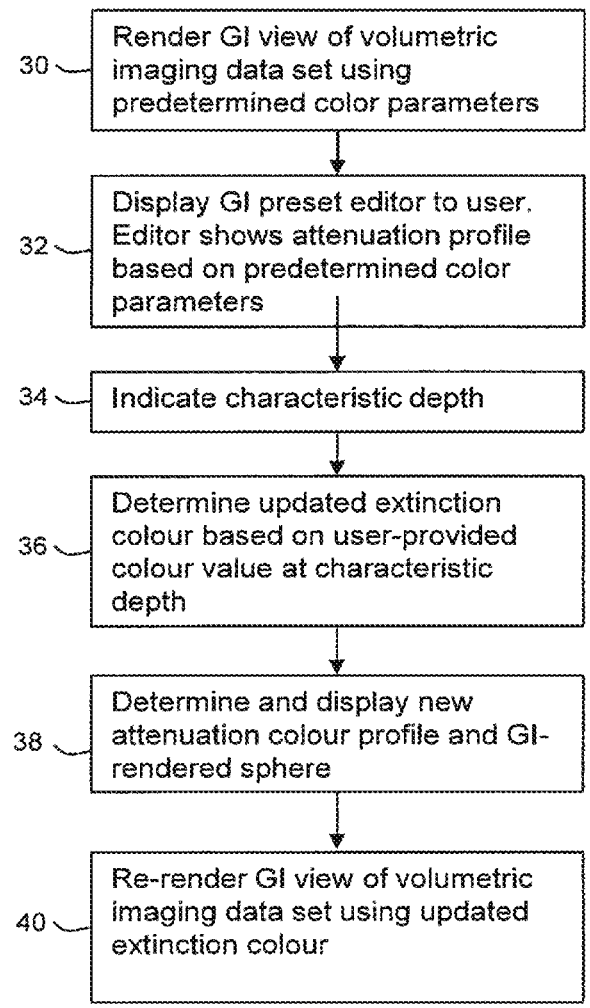
FIG. 2 is a flow chart illustrating in overview a method of an embodiment.

The apparatus of FIG. 1 is configured to perform a series of stages as illustrated in overview in the flow chart of FIG. 2.

At stage 30 of FIG. 2, the rendering circuitry 24 renders a global illumination (GI) view of a set of volumetric imaging data. The set of volumetric imaging data is representative of a scan of a region of a patient or other subject. The region of the patient comprises one or more anatomical features, each formed of a respective material (for example, soft tissue, blood or bone).

In the present embodiment, the scan is a CT scan. In other embodiments, any suitable modality of data may be used.

Figure 3:
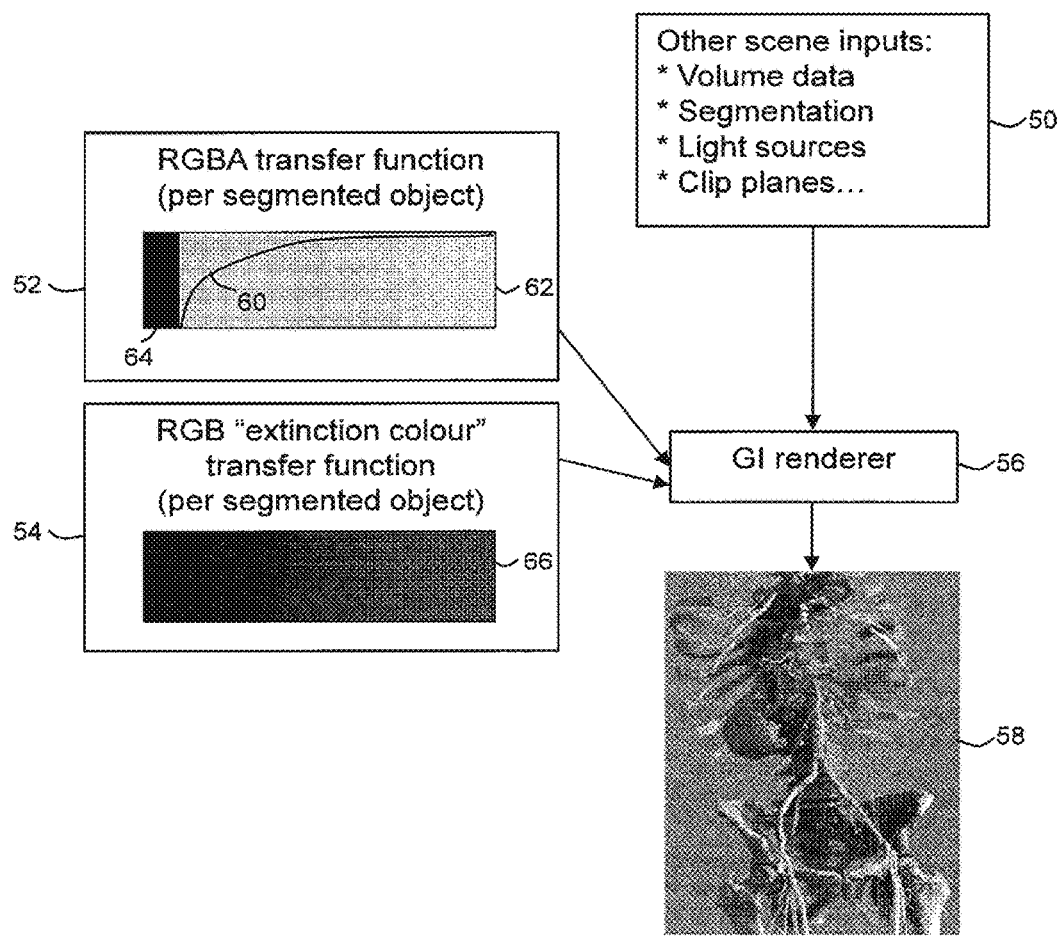
FIG. 3 is a flow chart illustrating in overview a method of an embodiment.

The rendering process of stage 30 is described in detail with reference to the flow chart of FIG. 3. In FIG. 3, the rendering process of stage 30 is broken down into sub-stages 50 to 58.

At sub-stage 50, the rendering circuitry 24 receives from data store 20 the set of volumetric imaging data that is to be rendered. In other embodiments, the rendering circuitry 24 receives the volumetric imaging data set from a remote data store or from the scanner 14 directly.

The rendering circuitry 24 also receives from data store 20 (or from another data store) a set of segmentation data. The set of segmentation data represents a segmentation of at least part of the volumetric imaging data set. In further embodiments, the rendering circuitry 24 is configured to obtain the set of segmentation data by segmenting the volumetric imaging data set.

The segmentation of the volumetric imaging data set defines a plurality of segmented objects. Each segmented object is representative of a respective anatomical feature. The anatomical features may comprise, for example, organs, bones or vessels.

The rendering circuitry 24 also receives from data store 20 (or from another data store) a set of scene inputs. The scene inputs may comprise, for example, positions of one or more light sources and/or positions of one or more clip planes. The scene inputs may comprise, for example, segmented regions and/or mesh geometry. In further embodiments, the rendering circuitry 24 is configured to determine the set of scene inputs. For example, the rendering circuitry 24 may be configured to determine the set of scene inputs based on user input.

At sub-stage 52, the rendering circuitry 24 receives a plurality of RGBA transfer functions from data store 20 (or from another data store). The plurality of RGBA transfer functions comprises a respective RGBA transfer function for each segmented object in the volumetric imaging data set. In alternative embodiments, the rendering circuitry 24 is configured to determine the RGBA transfer functions, for example based on user input.

Each RGBA transfer function defines a function of RGBA (red, green, blue, alpha) value against intensity value (which in this embodiment is CT value in Hounsfield units). Each RGBA value may be described as a DVR color. Each RGBA transfer function may be stored in any suitable manner, for example as a look-up table. The RGBA transfer function may be considered to comprise three color channels, each representative of a respective one of color components R, G, B, and an opacity channel.

An example of an RGBA transfer function for a segmented object is represented in FIG. 3 as a opacity curve 60 overlaying a color ramp 62, which may be referred to as a DVR color ramp. A DVR color ramp may be derived from color-picked control points. The opacity curve 60 is representative of opacity (alpha) against intensity (CT value). The color ramp 62 is representative of color against intensity.

Opacity curve 60 plots opacity on a vertical axis on which 0% opacity is at the bottom of the vertical axis, increasing to 100% opacity at the top of the vertical axis. Intensity is plotted on the horizontal axis. In the example shown, a region at the left side of the horizontal axis (representative of a set of low values of intensity) may be referred to as a null region 64. The null region 64 comprises values of intensity for which opacity is 0% (fully transparent). At intensity values above those of null region 64, opacity increases with intensity and then plateaus.

Color ramp 62 shows RGB color values which change with intensity value (intensity is shown on the same scale as for the opacity value). In the null region 64, no color is defined, because opacity is 0% and therefore voxels having intensities in the null region 64 are fully transparent. Above the null region, the color ramp shades from a pinker color to a yellower color as intensity increases. (Since FIG. 3 is shown in greyscale, the pinker to yellower color change is not visible in FIG. 3.) The RGB values of the color ramp 62 may alternatively be defined and/or stored in any suitable color format, for example HSV (hue, saturation, value).

In the present embodiment, each segmented object in the volumetric imaging data set is associated with a respective RGBA transfer function. Different anatomical structures may be associated with different colors, and therefore with different transfer functions. In some embodiments, all anatomical structures that comprise the same material (for example, all vessels) are associated with the same RGBA transfer function, so that all anatomical structures comprising that material are rendered in the same color or colors. Colors used in the RGBA transfer functions may be intended to provide a realistic coloring, or to provide a false color view, for example a false color view in which objects of similar tissue types may be visually distinguished in the image. Colors may vary with intensity in any suitable manner.

At sub-stage 54, the color circuitry 26 determines a respective RGB extinction color transfer function for each of the segmented objects. For each segmented object, the color circuitry 26 determines the RGB extinction color transfer function for that object based on the RGBA transfer function for that object that was received at stage 52.

We consider one of the segmented objects, which has an associated RGBA transfer function which represents color and opacity as a function of intensity value.

For each intensity value, the color circuitry 26 determines an extinction color component for each channel c (for c=each of R, G and B) using the equation:

$$\text{Extinction color}_c = 1 - (1-a)\char`\^(1-c) \quad \text{(Equation 1)}$$

where a is the opacity value for that intensity value, and c is the color component value (value for R, G or B) for that intensity value. Values for a and c are obtained using the RGBA transfer function.

The extinction color components Extinction color$_{c=R,G,B}$ are combined to give an RGB extinction color value for each intensity value. The RGB extinction color for each intensity value is a measure of color that is absorbed as light passes through a material having that intensity value. The RGB extinction color determined using Equation 1 may be described as a theoretically derived extinction color.

Theoretically derived extinction color is related to DVR color, which may be an RGBA value. However, unlike DVR color, the extinction color may not resemble any color that is present in a rendered image of the segmented object. For example, for a segmented object having a pink or beige DVR color, the extinction color may be blue.

Extinction color ramp 66 plots extinction color against intensity value for a segmented object (the same segmented object that is represented by opacity curve 60 and DVR color ramp 62). Extinction color varies from a darker blue at the left (low intensity) end of extinction color ramp 66 to a lighter blue at the right (high intensity) end of extinction color ramp 66. In general, extinction color may vary with intensity in any suitable manner.

In the present embodiment, the RGB extinction color transfer function for each segmented object is determined automatically by the color circuitry 26 using Equation 1. The rendering circuitry 24 receives the RGB extinction color transfer functions from the color circuitry 26. In other embodiments, the RGB extinction color transfer functions are received by the rendering circuitry 24 from data store 20 or from another data store. The RBG extinction color transfer functions may be determined based on user input. In some embodiments, the RGB extinction color transfer functions are not dependent on the RGBA transfer functions.

At sub-stage 56 of the flow chart of FIG. 3, the rendering circuitry 24 renders an image from the volumetric imaging data set using the data that was received at sub-stage 50, the RGBA transfer functions for each segmented object that were received at sub-stage 52, and the RGB extinction color transfer functions for each segmented object that were received at sub-stage 54. The rendering circuitry 24 renders the image using a global illumination rendering method. Any suitable global illumination rendering method may be used.

At sub-stage 58, the display circuitry 28 displays the rendered image on display screen 16, where it is viewed by a user. Sub-stage 58 of FIG. 3 completes the image rendering process of stage 30 of FIG. 2.

Returning to FIG. 2, at stage 32 the display circuitry 28 displays an editing interface on display screen 16. In the present embodiment, the editing interface is displayed alongside the rendered image on display screen 16. In other embodiments, the rendered image and the editing interface may be displayed on different display devices, for example on different display screens.

Figure 4:
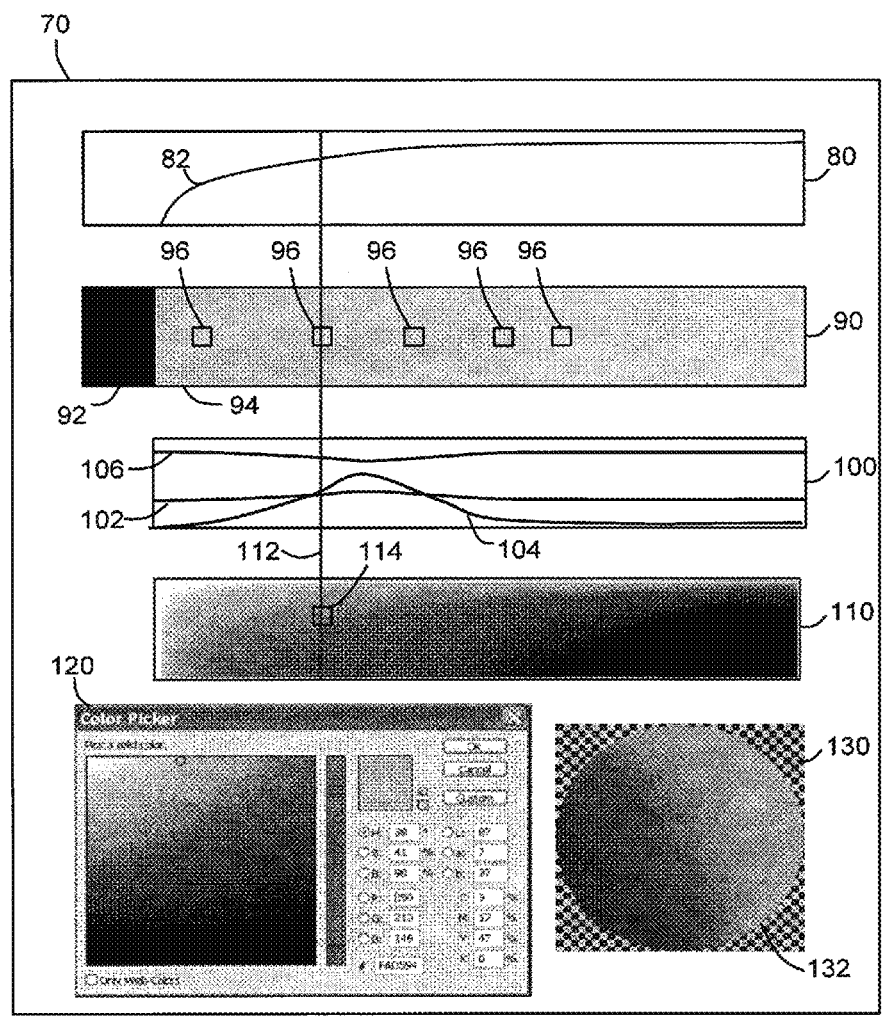
FIG. 4 is a schematic illustration of a GI color preset editor.

In the present embodiment, the editing interface may be referred to as a GI preset editor screen 70. An example of a GI preset editor screen 70 of the present embodiment is shown in FIG. 4. The GI preset editor screen 70 allows a user allows a user to edit parameters associated with a single segmented object of the volumetric imaging data set.

In the present embodiment, the display circuitry 28 is configured to display a respective GI preset editor screen 70 for each of a plurality of different segmented objects in the volumetric imaging data set. The GI preset editor screens 70 may be displayed concurrently or sequentially. The GI preset editor screens 70 may be displayed at the request of the user.

For simplicity, the flow chart of FIG. 2 describes an example of use of a single GI preset editor screen 70 to alter parameters relating to a single segmented object. In practice, a user may alter parameters relating to several different segmented objects by providing input on one or more GI present editor screens 70. For example, stages 32 to 40 of FIG. 2 may be repeated for each of a plurality of segmented objects, each having a respective GI preset editor screen 70.

GI preset editor screen 70 comprises an opacity curve editor 80, DVR color ramp editor 90, extinction color modulation plot 100, attenuation color profile 110, color picker 120 and sphere preview 130. In other embodiments, an editing interface may not include all of the individual components 80, 90, 100, 110, 120, 130 of GI preset editor screen 70. An editing interface may include additional components that are not shown in FIG. 4.

In the present embodiment, a user may use one or more of the opacity curve editor 80, DVR color ramp editor 90, extinction color modulation plot 100, attenuation color profile 110, color picker 120 and sphere preview 130 to change one or more rendering parameters used to render an image from the volumetric imaging data set.

In the example of a GI preset editor screen 70 shown in FIG. 4, the opacity curve 82 shown on opacity curve editor 80 is the same as the opacity curve 60 shown in FIG. 3. Low CT values are fully transparent. Once a threshold CT value is reached, opacity values increase with CT value before eventually levelling off.

The opacity curve editor 80 is configured such that a user may adjust the opacity curve 82, for example by changing the position of one or more points on the opacity curve 82. If the user changes the position of one or more points on the opacity curve 82, the color circuitry 26 may interpolate or extrapolate the changed opacity to other CT values. In some embodiments, the color circuitry 26 may also determine modified values for extinction color based on the adjustments to opacity made by the user. For example, the color circuitry 26 may calculate modified values for one or more extinction colors by using Equation 1 with the new opacity values resulting from the user adjustment.

The DVR color ramp editor 90 comprises a DVR color ramp 94. In the present embodiment, the DVR color ramp 94 comprises a null region 92 in which opacity is 0%. In the present embodiment, the DVR color ramp 94 shown on DVR color ramp editor 90 is the same as the DVR color ramp 62 shown in FIG. 3. DVR color changes with CT value in the segmented object of interest.

The DVR color ramp editor 90 is configured such that a user may adjust one or more color of the DVR color ramp 94 by changing the color at one or more of a plurality of selection points 96. A selection point 96 may be placed at any intensity value.

In one example, the user selects a color at a selection point 96 using color picker 120 or using any other suitable method. Color picker 120 allows a color to be selected by clicking a color on a display of colors or by typing in numerical values, for example RGB values, HSB (hue, saturation, brightness) values, CMYK (cyan, magenta, yellow, key) values, or Lab (lightness, red-green, yellow-blue) values. The color circuitry 26 replaces the original color at the selection point 96 with the user-selected color value. The color circuitry 26 may interpolate or extrapolate user-selected colors to obtain a modified DVR color ramp comprising a respective color for each CT value. For example, the color circuitry 26 may interpolate or extrapolate user-selected colors to obtain a smooth transition of color with intensity.

In some embodiments, the opacity curve editor 80 and DVR color ramp editor 90 may be similar to the opacity curve editor 80 and DVR color ramp editor 90 provided in some known rendering systems. Any appropriate preset editor controlling an opacity curve and conventional DVR material color (as a function of CT value and segmented object) may be used.

The extinction color modulation plot 100 of the GI preset editor screen 70 of FIG. 4 represents extinction color using HSV values. In the present embodiment, no extinction color ramp (for example, as shown in extinction color ramp 66 of FIG. 3) is included in the GI preset editor screen 70. Therefore, a user does not see the extinction color as a rendered color (for example, blue). In extinction color modulation plot 100, H, S and V values for extinction color are represented by lines 102, 104 and 106 respectively. The HSV values correspond to the extinction colors shown in the RGB extinction color transfer function 66 of stage 54 of FIG. 3.

In the present embodiment, a user may change extinction color values by moving one or more points on the extinction color modulation plot 100. The color circuitry 26 may interpolate or extrapolate changed extinction color values for one or more intensity values to obtain changed extinction color values for other intensity values.

An extinction color for a material gives rise to a color gradient through a material (if the material is not fully transparent or fully opaque). When light passes into the material, some of the light is absorbed. The color in the material changes in dependence on the accumulated opacity. As depth into the material increases, color becomes darker as light is absorbed.

Depth into the material is a distance which may be expressed, for example, in meters or in millimeters. In some embodiments, depth is expressed in voxels, where the distance is relative to the resolution of the acquisition.

A color gradient due to an extinction color may be referred to as a chromatic attenuation ramp. A chromatic attenuation profile may comprise one or more color attenuation ramps (for example, a set of color attenuation ramps for different intensity values). A chromatic attenuation profile may be representative of color as a function of depth in a material. The chromatic attenuation profile may also be representative of color as a function of intensity.

In the present embodiment, the attenuation profile preview 110 of the GI preset editor screen 70 of FIG. 4 displays a chromatic attenuation profile comprising a color gradient for each CT value in the range of CT values for which extinction colors have been determined.

The X axis of the chromatic attenuation profile is CT value. The Y axis of the chromatic attenuation profile is depth into homogeneous material of that value. Adding an attenuation profile to the GI preset editor screen 70 may provide a user with insight into how a material's extinction color affects incoming illumination.

For each CT value, a vertical line taken through the chromatic attenuation profile at that CT value is representative of color with depth in a homogeneous material having that CT value (and its associated opacity, DVR color and extinction color). The surface of the material is represented by the top of the vertical axis, with depth increasing downwards.

The attenuation profile preview 110 therefore shows variation of a color of a material of the segmented object with intensity value (from left to right) and also shows variation of the color of the material with depth into an object formed of that material (from top to bottom). In the present embodiment, the color of the chromatic attenuation profile of attenuation profile preview 110 is red, becoming darker from top to bottom, and browner from left to right. However, FIG. 4 is shown as a greyscale version.

Attenuation profile preview 110 may provide an alternative method of adjusting extinction color, which may be more intuitive than adjusting the extinction color directly (for example, adjusting the HSV values of extinction color modulation plot 100).

The attenuation profile preview 110 is configured such that the user may adjust a color at any point of the chromatic attenuation profile, i.e. for any pair of values of depth and intensity. The color circuitry 26 uses the adjusted color to determine a modified extinction color. For example, if the user adjusts a color at a given depth, the color circuitry 26 may determine the extinction color that would be needed to provide that color at that depth. The color circuitry 26 may interpolate or extrapolate one or more colors adjusted by the user to obtain further modified extinction colors.

It has been found that users may find extinction color difficult to work with, for example because the extinction color does not resemble a color of tissue that is rendered using the extinction color. Therefore, if the user wishes to edit an extinction color, the user may find it easier to edit a color of the attenuation profile preview 110, allowing the extinction color to be determined by the color circuitry 26 rather than by the user directly.

In the present embodiment, the display circuitry 28 also displays on the attenuation profile preview 110 one or more indicators 114 that indicate a characteristic depth into the material. The indicators and the characteristic depth are described further below with reference to stage 34.

Color picker 120 of the GI preset editor screen 70 of FIG. 4 may be used by the user to pick a color for the DVR color ramp 94 or for the chromatic attenuation profile of attenuation profile preview 110. Color may be selected by selecting a color from a color display or by typing in a color value.

Sphere preview 130 of the GI preset editor screen 70 of FIG. 4 is an image of a GI-rendered sphere of substantially homogeneous material having a given CT value. In the present embodiment, a GI-rendered sphere is rendered by the rendering circuitry 24 as a homogeneous object having the opacity, DVR color and extinction color associated with the selected CT value. The opacity, DVR color and extinction color are each constant throughout the object, since the object is formed of homogeneous material of a single intensity value. The sphere preview 130 previews a material with volumetric lighting.

Displaying a GI-rendered sphere of substantially homogeneous material for a given CT value may give a user more insight into the result of properties they have selected for that CT value. By showing a GI-rendered sphere, the user may be able to assess color better than by viewing the attenuation profile alone. In some circumstances, it may be quicker to render the GI-rendered sphere using the modified extinction color than to render an image using the modified extinction color. The sphere may therefore be used as a preview.

In other embodiments, any predetermined shape or shapes may be rendered, which may or may not include a sphere. The predetermined shape or shapes may be selected by a user. The predetermined shape may be pre-stored.

In some embodiments, the intensity value for which the sphere is rendered is automatically determined by the rendering circuitry 24. In some embodiments, the intensity value for which the sphere is rendered is selected by a user. In some embodiments, a pre-stored intensity value is used.

In some embodiments, previews of one or more tubular structures may be displayed. Previews of structures (for example, tubular structures) of different thicknesses may be displayed. Previewing tubular structures may allow the user to assess how tubular or near-tubular structures (for example, vessels) may look when rendered using the current set of rendering parameters for the selected intensity value, for example using the current extinction color.

Structures may be displayed that are at different angles to a light source. Spheres (or other shapes) of substantially homogeneous materials may be rendered with a GI algorithm and various material properties and light source directions.

Returning to the flow chart of FIG. 2, an image has been rendered at stage 30 using the process of FIG. 3, and the GI preset editor screen 70 of FIG. 4 has been displayed to a user at stage 32.

The flow chart of FIG. 2 then proceeds to stage 34. At stage 34, the user selects a CT value. The selected CT value is represented on FIG. 4 by line 112. The color circuitry 26 displays an indicator 114 on the attenuation color profile 110 for that CT value. The indicator 114 is displayed at a position that is representative of a characteristic depth in the material.

A homogeneous material of a single CT value has a single extinction color throughout the material. However, due to chromatic attenuation, the single extinction color yields a changing color through the material. For example, a color of light passing through a material may become redder as it passes through more of the material.

For each CT value, the opacity value for that CT value defines a characteristic distance at which a given proportion of light has been absorbed by the material. In the present embodiment, the characteristic distance is the 50% accumulated attenuation point. The 50% accumulated attenuation point is a point at which 50% of light has been attenuated.

The indicator 114 is displayed at the characteristic depth for the CT value of line 112, i.e. the point on line 112 that is representative of a depth at which 50% of light has been attenuated.

Opacity may be defined as a fraction of absorption over distance. The fraction of absorption may be expressed without unit since it may be defined as follows: (original intensity in lumen−transmitted intensity in lumen)/(original intensity in lumen). Opacity may therefore be expressed in units of 1/distance.

The characteristic depth d at which an accumulated opacity k is reached is the solution of $$1-(1-a)^d=k \quad \text{(Equation 2)}$$

for a homogeneous material in which the opacity is a and d is the distance into the material. Therefore $$d=\log(1-k)/\log(1-a) \quad \text{(Equation 3)}$$

Characteristic depth varies with opacity. For example, in the present embodiment the characteristic depth is defined as the 50% accumulated attenuation point, k=0.5. If opacity a is 0.8, the characteristic depth d is 0.43. If opacity a is 0.9, the characteristic depth d is 0.33. If opacity a is 0.99, the characteristic depth d is 0.15. For a more opaque material, the characteristic depth d is nearer the surface than in the case of a less opaque material. Therefore, the vertical position of the characteristic depth indicator 114 is dependent on the opacity at the selected CT value.

In Equations 2 and 3 above, characteristic depth d is calculated using accumulated opacity. It is possible to derive Equations 2 and 3 from the Beer-Lambert law. In embodiments, attenuation may be expressed as an attenuation coefficient and/or as an opacity. Opacity may be expressed as a fraction from [0,1] while an attenuation coefficient may be defined over [0, ∞].

A transmission T may represent how much intensity remains. For a constant attenuation coefficient μ, the transmission T over a distance l is:

$$T=e^{-\mu l} \quad \text{(Equation 4)}$$

Since the opacity is the attenuation over a unit distance, it is possible to convert from one of attenuation and opacity using the other of attenuation and opacity by setting l=1, resulting in the following equation:

$$(1-a)=e^{-\mu} \quad \text{(Equation 5)}$$

In the example where k=0.5 and a=0.8, opacity can be converted to an attenuation coefficient as follows:

$$(1-0.8)=e^{-\mu} \quad \text{(Equation 6)}$$

$$\mu=\log(5)\approx 1.6094 \quad \text{(Equation 7)}$$

The distance d can then be expressed using the Beer-Lambert law $$(1-0.5)=e^{\log(5)d} \quad \text{(Equation 8)}$$

Solving Equation 8 for d also gives d≈0.43. In further embodiments, any suitable method of calculating characteristic depth may be used.

In some circumstances, the point at which the light has been attenuated by half may be close to a color that may be seen in a final rendering. At the surface of an object, color may not have built up. A 50% attenuation point may be considered to be representative of the color of the object. In other embodiments, a different characteristic depth may be used, for example a depth at which a different proportion of the light has been absorbed.

In some circumstances, color at 50% attenuation may be fairly consistent even when different opacity values are used, so may give a stable parameter.

At stage 36, the user selects a modified color c* at the position shown by the indicator 114 (which is the characteristic depth at the selected CT value). The color circuitry 26 calculates a modified extinction color c' based on the modified color c*.

A relation between extinction color c' and attenuated color c* at characteristic depth d is:

$$c^*=c'^d \quad \text{(Equation 9)}$$

Therefore:

$$c^*=c'^{(\log(1-a)/\log(1-k))} \quad \text{(Equation 10)}$$

Given a user-modified c*, Equation 10 may be inverted by the color circuitry 26 to obtain a modified extinction color:

$$c'=c^{*(\log(1-a)/\log(1-k))} \quad \text{(Equation 11).}$$

In further embodiments, any suitable method of calculating a modified extinction color may be used.

At stage 38 of FIG. 2, the rendering circuitry 24 re-renders the sphere preview 130 using the selected CT value and the modified extinction color c'. The display circuitry 28 displays the re-rendered sphere preview 130.

The color circuitry 26 uses the modified extinction color c' at the selected CT value to determine a modified attenuation profile preview 110. The color circuitry 26 may interpolate or extrapolate the modified extinction color c' calculated from the color value supplied by the user to obtain extinction colors for other CT values and modify the attenuation profile preview 110 accordingly for those CT values.

The color circuitry 26 may also determine a modified extinction color modulation plot 100 that displays the modified extinction colors.

The color selection of stages 34 and extinction color modification of stage 36 may be repeated at several different points on the attenuation profile preview 110. In one embodiment, the user selects successively several different CT values. For each CT value, the display circuitry 28 displays an indicator 114 at the characteristic depth for that CT value, and the user selects a color at the indicated characteristic depth. The color circuitry 26 uses the user-selected colors to determine extinction colors for the selected CT values. The color circuitry 26 extrapolates and interpolates extinction color values from the selected CT values to other CT values in the attenuation profile preview. The display circuitry 28 displays the modified attenuation profile preview 110 and modified extinction color modulation plot 100.

At stage 40, the rendering circuitry 24 re-renders the image from the volumetric imaging data set using the modified extinction color value. In some embodiments, the rendering circuitry 24 obtains confirmation from the user of the colors to be used before re-rendering the image. The user may repeatedly change the colors to be used before proceeding to re-rendering.

Figure 5:
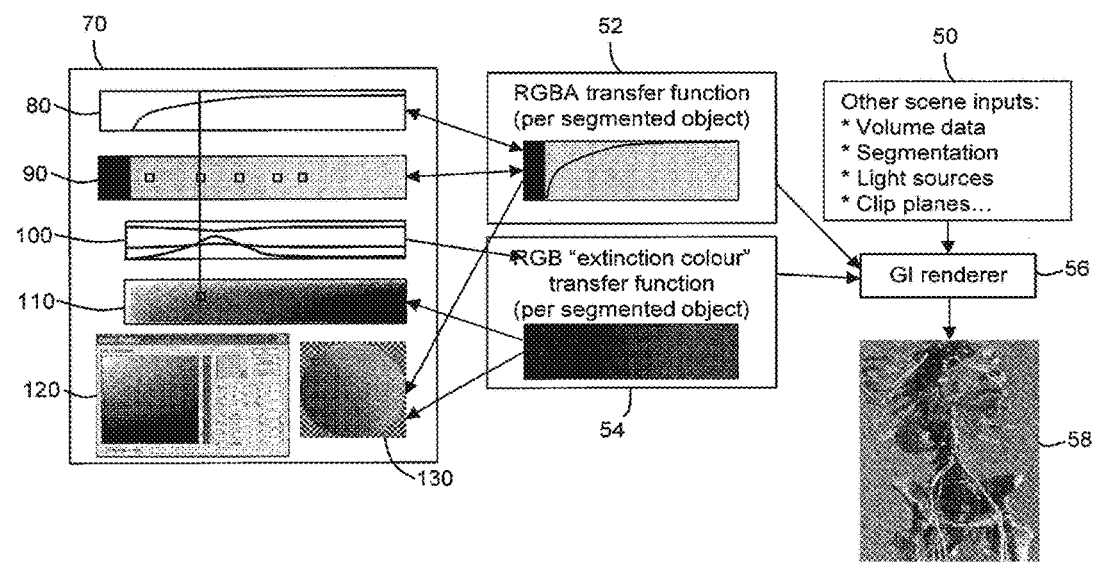
FIG. 5 is a flow chart illustrating in overview a method of an embodiment.

FIG. 5 shows an overview of some ways in which changes made using GI preset editor screen 70 may interact with a rendering process similar to that described with reference to FIG. 3. Interactions are shown by arrows.

Changes made using opacity editor 80 or DVR color ramp editor 90 may affect the RGBA transfer functions of stage 52. Changes in the RGBA transfer function of stage 52 may affect what is displayed in the opacity editor 80 or DVR color ramp editor 90 and/or may affect sphere preview 130.

Changes made to extinction color using the extinction color modulation plot 100 may affect the RGB extinction color transfer functions of stage 54. Changes to the RGB extinction color transfer functions of stage 54 may affect the attenuation color profile preview 110 and/or sphere preview 130.

In the embodiment described above with reference to FIG. 2, the user modifies extinction color for a given CT value by selecting a color at a characteristic depth. In other embodiments, the user may change extinction color by adjusting one or more H, S or V values on the extinction color modulation plot 100.

Theoretically, the RGB extinction color may be related to RGBA DVR color as described above with relation to FIG. 1. In the present embodiment, RGB extinction color is initially calculated based on RGBA DVR color.

However, in practice it may be useful for a user to be able to provide manual adjustments to the theoretical extinction color. Providing manual adjustments to the theoretical extinction color may be used to achieve subtle image effects.

In some embodiments, user control of extinction color is specified in terms of modulation of HSV values or other color spaces, for example other color spaces that are considered to be intuitive. A color variation may be defined in terms of the impact on the color at the characteristic depth.

In some embodiments, a user picks a DVR color and opacity for a given intensity value. The color circuitry 26 computes an extinction color corresponding to the DVR color using Equation 1. The extinction color itself (for example, blue) is not displayed as a rendered color. The extinction color may be considered not to be of interest to non-experts.

The user observes the resulting attenuation profile using attenuation profile preview 110. The user expresses one or more desired colors of the attenuation profile in terms of HSV tweaks to existing colors in the attenuation profile (for example, a hue shift or value or saturation boost). The color modulation specified by the user is considered to apply at the characteristic depth for the opacity at the relevant intensity value.

The user may move a dial or slider to change some specific feature of the colors, for example to make one or more colors redder or more saturated or lighter.

The color circuitry 26 recomputes the extinction color to yield a modified extinction color. The modified extinction color may be different from the theoretically derived extinction color that was originally obtained using Equation 1. The user sees the modified attenuation profile in the preset editor. The user may also see an updated rendering.

Adjusting extinction colors by adjusting colors in the attenuation profile may provide an intuitive method for adjusting extinction colors. Users may be familiar with a system in which they may be able to nudge a preset (for example, preset colorings) up and down in HU values. The present embodiment may provide similar functionality with respect to extinction colors. In some embodiments, a user may want to adjust a preset function only at certain locations.

Defining the modification of colors in terms of an offset of hue, saturation or value (or of other color components) may allow the modification to be retained even when a DVR RGBA value is updated. In some circumstances, manual override of automatically computed extinction colors may be overwritten when DVR RGBA colors are updated. However, in some embodiments, H, S or V adjustments are stored as offset parameters and the offset parameters are applied even when an original DVR value is changed. For example, if the user chooses that an extinction color should result in a more saturation attenuation profile color than would be the case with the theoretical extinction color, this increased saturation may be maintained even if the user then changes the DVR value.

In further embodiments, offsets (for example, H, S, or V offsets) of the extinction color are stored and those offsets to the extinction color are applied when DVR color is adjusted.

Automatic color may be combined with manual modifications.

Embodiments described above may provide a user with an intuitive method of controlling extinction color, which may allow extinction colors to be used that are different from those derived from DVR color using Equation 1.

Experience with allowing preset designers completely independent control over extinction color suggests that preset designers may find extinction color hard to work with. Extinction color may appear to behave counterintuitively. For example, a user who is unfamiliar with the inner workings of GI and the underlying theory of GI may find the effects of adjusting extinction color to be counterintuitive.

In some circumstances, it may be valuable for users to manually vary extinction color away from a theoretical value for extinction color. However, the user may find it difficult or frustrating to adjust an extinction color that may not resemble any color in the resulting rendered image.

Visualizing an extinction color directly may not be useful to most useful as the extinction color may never appear in the rendered image. It has been found that an inverse of the extinction color, while being somewhat similar to the DVR color, may not provide an accurate match to the DVR color.

In embodiments described above, the extinction color itself is not displayed to the user as a color. Instead, the attenuation profile preview 110 shows a change in color with depth into the material. The extinction color gives rise to the chromatic attenuation color gradient through material.

The color gradient may be more meaningful to the user than a display of the extinction color itself. For example, the attenuation profile preview 110 may show a red gradient rather than a blue extinction color. By displaying the gradient at each CT value, the user may have better information about the impact of the extinction color than if the extinction color itself were to be displayed.

In some embodiments, instead of controlling extinction color directly (for example, by selecting an extinction color), the user controls a color in the attenuation profile that results from the extinction color. In some embodiments, the user may alternatively or additionally adjust extinction color using an extinction color modulation plot 100 or other extinction color display.

If a user wants to exercise control over extinction color, controlling extinction color directly may be frustrating for similar reasons to why it may not be useful to display the extinction color directly. While the extinction color is constant for homogeneous material, due to chromatic attenuation it yields a changing color through that material. Therefore it may not be clear what picking a single color should actually be selecting. By defining a characteristic distance for each CT value (for example, the 50% accumulated attenuation point), a distance at which the color is to be controlled may be provided to the user. Providing the characteristic distance may make it easier for a user to control extinction color.

Color may be controlled at a characteristic distance. The color at the characteristic distance may be considered to be representative of a color of a rendered object.

The display of an attenuation profile may be used whether extinction color is completely automatic, or manually controlled, or a hybrid. For example, even in embodiments in which extinction color is derived from DVR color without user input, it may still be useful for the user to see the attenuation profile. The display of a homogeneous object at a particular CT value may also be useful whether the control of extinction color is automatic, manual, or a hybrid.

The GI preset editor screen 70 may provide several user interface (UI) additions to preset editing dialogs that may make GI editing easier. Extinction color modulation may be provided. An attenuation profile preview may be derived from extinction color. 'Color at depth' color picking may be used. A homogeneous material preview may be displayed.

Certain embodiments provide a system with global illumination and color preset (transfer function) editing in which a preview of a chromatic attenuation profile is displayed in an editor.

Certain embodiments provide a system with global illumination and color preset (transfer function) editing in which color picking of an extinction color is performed at a particular depth in an attenuation profile.

Certain embodiments provide a system with global illumination rendering and color preset (transfer function) editing in which the editor displays a preview of a sphere (or of another shape, for example a cylinder) of solid material of a current material of interest.

Certain embodiments provide a system with global illumination rendering and color preset (transfer function) editing in which an extinction color automatically derived from a conventional DVR color can be manually adjusted. The manual adjustment may be by modulation of hue, saturation and/or value.

Combinations and variants of the above embodiments may be provided.

In the embodiments described above, opacity is used. Opacity is a parameter that may refer to scattering and absorption. In other embodiments, one or more alternative parameters may be used to quantify scattering, absorption or other lighting parameters.

In the embodiments described above, the volumetric imaging data set comprises CT data. In other embodiments, the volumetric imaging data set may comprise data of any appropriate modality, for example, cone-beam CT, MRI, X-ray, PET, SPECT or ultrasound data.

The volumetric imaging data set may be representative of any appropriate anatomical region of any human or animal subject. Any suitable global illumination rendering method may be used. Any suitable display system and method may be used. The user may provide input through any suitable user input interface.

The method of FIGS. 2, 3 and 5 may be provided on any suitable image processing apparatus, which may or may not be coupled to a scanner. The apparatus may be used for post-processing data. The data may be stored data.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An image rendering apparatus, comprising:
   processing circuitry configured to
      obtain a volumetric medical imaging data set representative of a region of a selected type of tissue;
      associate one particular extinction color with the selected type of tissue;
      determine, based on the one particular extinction color, a chromatic attenuation profile representative of color values as a function of both intensity and depth in the selected type of tissue, the chromatic attenuation profile including a plurality of points defined for a range of depths and a range of intensities and showing how a rendering of a homogeneous region of the selected type of tissue, having the one particular extinction color, would change in appearance with changes in the depth of the selected type of tissue as a result of illumination by a virtual light source;
      display, to a user, the determined chromatic attenuation profile;
      obtain, from the user, a modified color value for a particular point in the displayed chromatic attenuation profile, the particular point being determined by input from the user;
      calculate a modified extinction color for the selected type of tissue based on the particular point and the obtained modified color value for the particular point in the displayed chromatic attenuation profile; and render a global illumination image from the volumetric medical imaging data set using the modified extinction color.

2. The apparatus according to claim 1, wherein the processing circuitry is further configured to determine the chromatic attenuation profile by, for each of a plurality of depths in the selected type of tissue, determining a corresponding color value at that depth, based on an accumulated opacity of the selected type of tissue at that depth.

3. The apparatus according to claim 2, wherein the processing circuitry is further configured to determine a modified chromatic attenuation profile, based on the modified extinction color, and display the modified chromatic attenuation profile to the user.

4. The apparatus according to claim 3, wherein the processing circuitry is further configured to determine the modified extinction color by determining a first modified extinction color for a first intensity value, and interpolating or extrapolating the first modified extinction color at the first intensity value to obtain a modified extinction color for one or more further intensity values.

5. The apparatus according to claim 1, wherein the processing circuitry is further configured to obtain, from the user, the modified color value for the particular point on the displayed chromatic attenuation profile, the point being determined by a user-selected intensity and a determined depth; and
determine the modified extinction color based on the modified color value at the selected intensity and the determined depth.

6. The apparatus according to claim 1, wherein the processing circuitry is further configured to
determine and display, based on the chromatic attenuation profile, a characteristic depth in the material;
obtain, from the user, the modified color value for the characteristic depth; and
determine the modified extinction color based on the modified color value at the characteristic depth.

7. The apparatus according to claim 6, wherein the characteristic depth indicated by the processing circuitry is a depth at which a pre-determined proportion of light entering the selected type of tissue is attenuated by the selected type of tissue.

8. The apparatus according to claim 6, wherein the processing circuitry is further configured to calculate the modified extinction color based on the modified color value comprises using an equation:

$$c' = c^* \hat{\,} (\log(1-a)/\log(1-k))$$

wherein c' is the modified extinction color, c* is the modified color value, a is opacity, and k is accumulated opacity at the characteristic depth.

9. The apparatus according to claim 1, wherein the processing circuitry is further configured to render, using the extinction color or the modified extinction color, the global illumination image of a substantially homogeneous object formed of the selected type of tissue, the substantially homogeneous object having a predetermined shape and a constant intensity value.

10. The apparatus according to claim 9, wherein the predetermined shape comprises at least one of a sphere, a first tubular structure, and at least one further tubular structure having at least one of a different thickness, orientation, and angle of lighting than the first tubular structure.

11. The apparatus according to claim 9, wherein the processing circuitry is further configured to receive user input indicative of at least one of the predetermined shape and the constant intensity value.

12. The apparatus according to claim 1, wherein the processing circuitry is further configured to
display, to the user, at least one color value derived from the one particular extinction color;
obtain an adjustment of each displayed color value; and
determine the modified extinction color based on the at least one color value and the adjustment.

13. The apparatus according to claim 12, wherein the adjustment of each color value received from the user comprises an offset.

14. The apparatus according to claim 13, wherein the processing circuitry is further configured to apply the offset to at least one further color value to obtain at least one further extinction color.

15. The apparatus according to claim 1, wherein the processing circuitry is further configured to display, to a user, a user interface comprising at least one of the chromatic attenuation profile, an image of a substantially homogeneous object, and an extinction color modulation plot.

16. The apparatus according to claim 15, wherein the processing circuitry is further configured to obtain, via the user interface, a user input comprising at least one of the modified color value, a predetermined shape, and a constant intensity value.

17. The apparatus according to claim 1, wherein the processing circuitry is further configured to associate the one particular extinction color with the selected type of tissue by, for at least one intensity value of the selected type of tissue, obtaining a color and an opacity for the selected type of tissue at the at least one intensity value, and determining a corresponding extinction color at the at least one intensity value based on the obtained color and obtained opacity, wherein the determining of the one particular extinction color comprises using an equation:

$$\text{Extinction value}_c = 1 - (1-a)\hat{\,}(1-c)$$

wherein c is each of red, green, and blue, and a is opacity.

18. The apparatus according to claim 1, wherein the processing circuitry is further configured to associate the one particular extinction color with the selected type of tissue by using an extinction color transfer function for the selected type of tissue, the extinction color transfer function relating extinction color to intensity value.

19. The image rendering method, comprising:
obtaining a volumetric medical imaging data set representative of a region of a selected type of tissue;
associating one particular extinction color with the selected type of tissue;
determining, based on the one particular extinction color, a chromatic attenuation profile representative of color values as a function of both intensity and depth in the selected type of tissue, the chromatic attenuation profile including a plurality of points defined for a range of depths and a range of intensities and showing how a rendering of a homogeneous region of the selected type of tissue, having the one particular extinction color, would change in appearance with changes in the depth of the selected type of tissue as a result of illumination by a virtual light source;
displaying, to a user, the determined chromatic attenuation profile;
obtaining, from the user, a modified color value for a particular point in the displayed chromatic attenuation profile, the particular point being determined by input from the user;

calculating a modified extinction color for the selected type of tissue based on the particular point and the modified color value for the particular point in the displayed chromatic attenuation profile; and rendering a global illumination image from the volumetric medical imaging data set using the modified extinction color.

* * * * *